United States Patent
Ha et al.

(10) Patent No.: US 9,457,063 B2
(45) Date of Patent: Oct. 4, 2016

(54) METHOD FOR TREATMENT OF DIABETIC VASCULAR LEAKAGE-INDUCED DISEASE USING C-PEPTIDE

(71) Applicants: KANGWON NATIONAL UNIVERSITY UNIVERSITY-INDUSTRY COOPERATION FOUNDATION, Gangwon-Do (KR); AMOGREENTECH CO., LTD., Gyeonggi-do (KR)

(72) Inventors: Kwon-Soo Ha, Gangwon-Do (KR); Young-Cheol Lim, Gangwon-Do (KR)

(73) Assignees: KANGWON NATIONAL UNIVERSITY UNIVERSITY-INDUSTRY COOPERATION FOUNDATION, Gangwon-Do (KR); AMOGREENTECH CO., LTD., Gyeonggi-do (KR)

( * ) Notice: Subject to any disclaimer, the term of this patent is extended or adjusted under 35 U.S.C. 154(b) by 168 days.

(21) Appl. No.: 13/987,543

(22) Filed: Aug. 6, 2013

(65) Prior Publication Data

US 2014/0148386 A1    May 29, 2014

Related U.S. Application Data

(60) Provisional application No. 61/680,184, filed on Aug. 6, 2012.

(51) Int. Cl.
A61K 38/17    (2006.01)

(52) U.S. Cl.
CPC ............ *A61K 38/1709* (2013.01); *A61K 38/17* (2013.01); *A61K 38/1703* (2013.01)

(58) Field of Classification Search
CPC ............. A61K 38/17; A61K 38/1703; A61K 38/1709
See application file for complete search history.

(56) References Cited

U.S. PATENT DOCUMENTS 7,855,177 B1 *   12/2010   Wahren et al. ............... 514/5.9
2002/0077317 A1   6/2002   Das
2010/0292132 A1   11/2010  Bevec et al.

FOREIGN PATENT DOCUMENTS

KR    10-2010-0057640 A    5/2010
WO    WO 2005/039627 A2    5/2005
WO    WO 2009/068911 A1    6/2009

OTHER PUBLICATIONS

Ido et al. Prevention of vascular and neural dysfunction in diabetic rats by C-peptide. Science. 1997; 277: 563-566.*
B. -L. Johansson et al., "Beneficial effects of C-peptide on incipient nephropathy and neuropathy in patients with Type I diabetes mellitus," Diabetic Medicine, 2000.
Marjorie A. Mosier et al., "Circulating C-peptide and diabetic retinopathy," Diabetes Research, 1984.
Subrata Chakrabarti et al., "C-peptide and Retinal Microangiopathy in Diabetes," Experimental Diab. Res., 2004.
Bo-Lennart Johansson et al., "Influence of combined C-peptide and insulin administration on Renal Function and Metabolic Control in Diabetes Type 1," Journal of Clinical Endocrinology and Metabolism, 1993.
Ronald Klein et al., "Wisconsin Epidemiologic Study of Diabetic Retinopathy," Diabetes, 1990.
J. Wahren et al., "Does C-peptide Have a Physiological Role?", Diabetologia, vol. 37, No. Suppl. 2, 1994, pp. S99-S107.
S. Langer et al., "Effect of C-peptide on Wound Healing and Microcirculation in Diabetic Mice", European Journal of Medical Research, vol. 7, No. 11, Nov. 25, 2002, pp. 502-508.
John Wahren et al., "The Clinical Potential of C-Peptide Recplacement in Type 1 Diabetes," *Perspectives in Diabetes*, 2012.
P. Luippi et al., "C-peptide and long-term complications of diabetes," *Pediatric Diabetes*, 2011.

* cited by examiner

*Primary Examiner* — Prema Mertz
(74) *Attorney, Agent, or Firm* — Blank Rome LLP

(57) ABSTRACT

Disclosed is a method for the prevention or treatment of vascular leakage-induced diseases and diabetic retinopathy, using C-peptide. Found to prevent extravacular leakage by inhibiting VEGF-induced disassembly of VE-cadherin, C-peptide can be applied to the prevention or treatment of various diabetic complications accompanied by vascular leakage.

9 Claims, 13 Drawing Sheets

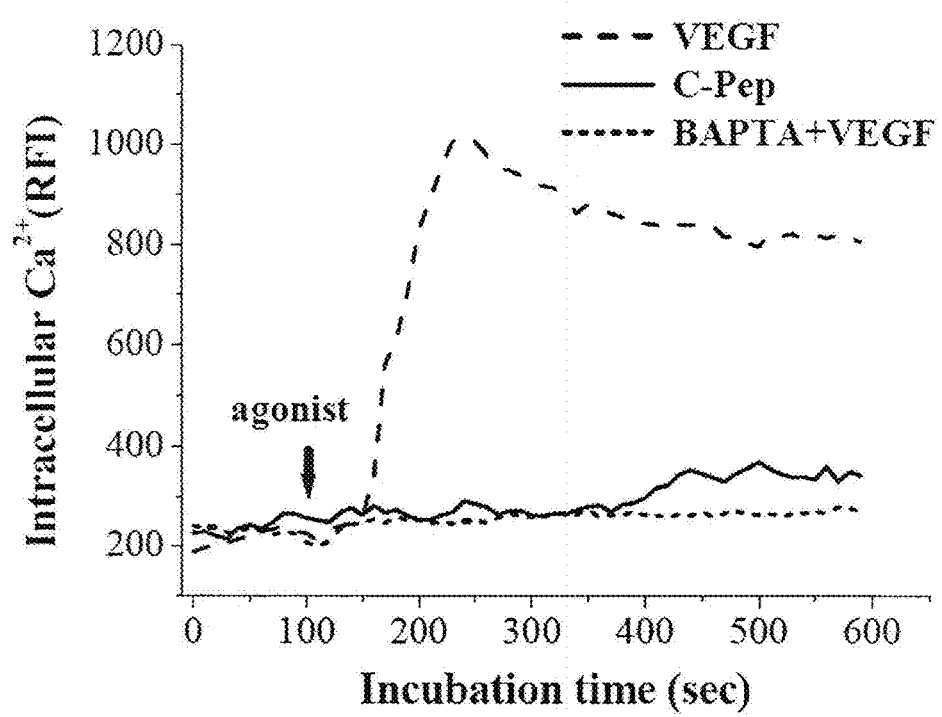

| Observations | Control | Diabetes | Diabetes + C-peptide |
|---|---|---|---|
| Serum C-peptide (nM) (at 1 week of diabetes induction) | 1.44±0.53 | 0.19±0.17*** | 0.18±0.15*** |
| Serum C-peptide (nM) (4 weeks after C-peptide delivery) | 1.50±0.89 | <0.1*** | 2.40±0.93 |

Data are means ± S.D. ***p<0.001 vs. control mice.

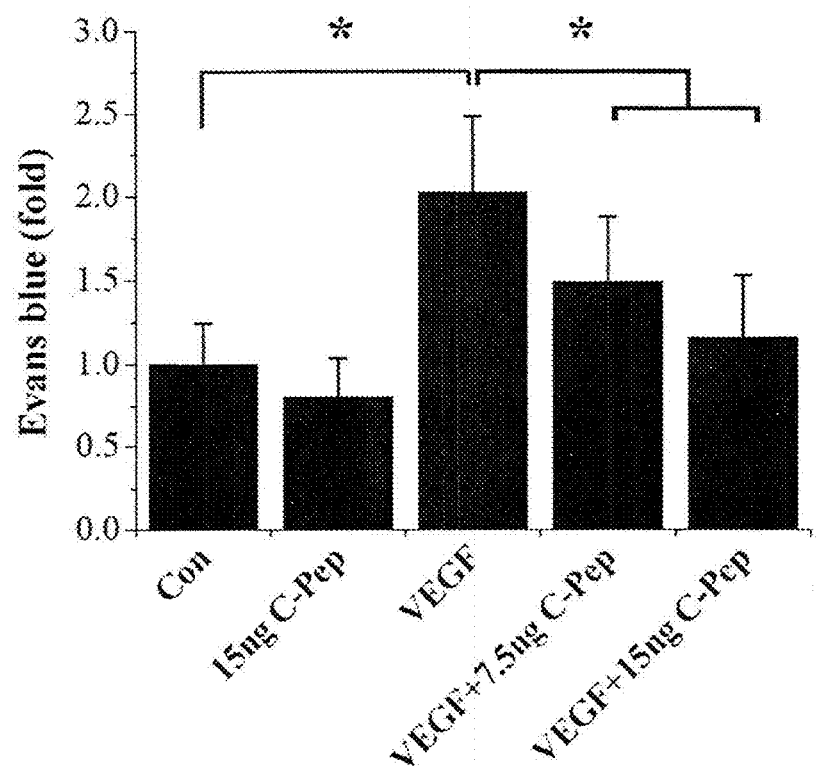

SEQUENCE LISTING

```
<160> NUMBER OF SEQ ID NOS: 7

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
 1               5                  10                  15

Gly Ala Gly Ser Leu Gln Pro Leu Ala Leu Glu Gly Ser Leu Gln
            20                  25                  30

<210> SEQ ID NO 2
<211> LENGTH: 31
<212> TYPE: PRT
<213> ORGANISM: Rattus norvegicus

<400> SEQUENCE: 2

Glu Val Glu Asp Pro Gln Val Pro Gln Leu Glu Leu Gly Gly Gly Pro
 1               5                  10                  15

Glu Ala Gly Asp Leu Gln Thr Leu Ala Leu Glu Val Ala Arg Gln
            20                  25                  30

<210> SEQ ID NO 3
<211> LENGTH: 31
<212> TYPE: PRT
<213> ORGANISM: Pan troglodytes

<400> SEQUENCE: 3

Glu Ala Glu Asp Leu Gln Val Gly Gln Val Glu Leu Gly Gly Gly Pro
 1               5                  10                  15

Gly Ala Gly Ser Leu Gln Pro Leu Ala Leu Glu Gly Ser Leu Gln
            20                  25                  30
```

```
<210> SEQ ID NO 4
<211> LENGTH: 29
<212> TYPE: PRT
<213> ORGANISM: Mus musculus

<400> SEQUENCE: 4

Glu Val Glu Asp Pro Gln Val Glu Gln Leu Glu Leu Gly Gly Ser Pro
 1               5                  10                  15

Gly Asp Leu Gln Thr Leu Ala Leu Glu Val Ala Arg Gln
            20                  25

<210> SEQ ID NO 5
<211> LENGTH: 26
<212> TYPE: PRT
<213> ORGANISM: Bos taurus

<400> SEQUENCE: 5

Glu Val Glu Gly Pro Gln Val Gly Ala Leu Glu Leu Ala Gly Gly Pro
 1               5                  10                  15

Gly Ala Gly Gly Leu Glu Gly Pro Pro Gln
            20                  25

<210> SEQ ID NO 6
<211> LENGTH: 21
<212> TYPE: PRT
<213> ORGANISM: Turdus merula

<400> SEQUENCE: 6

Ser Gly Pro Leu His Gly Glu Leu Gly Glu Leu Pro Phe Gln Gln Glu
 1               5                  10                  15

Glu Phe Glu Lys Val
            20

<210> SEQ ID NO 7
<211> LENGTH: 21
<212> TYPE: PRT
<213> ORGANISM: Sula sula

<400> SEQUENCE: 7

Ser Gly Pro Leu His Gly Glu Val Gly Glu Leu Pro Phe Gln Gln Glu
 1               5                  10                  15

Glu Phe Glu Lys Val
            20
```

METHOD FOR TREATMENT OF DIABETIC VASCULAR LEAKAGE-INDUCED DISEASE USING C-PEPTIDE

CROSS REFERENCE TO RELATED APPLICATION

This application claims the benefit of U.S. Patent Application Ser. No. 61/680,184, filed on Aug. 6, 2012, which is hereby incorporated by reference in its entirety into this application.

BACKGROUND OF THE INVENTION

1. Technical Field

The present invention relates to the prevention or treatment of diabetes-related diseases using C-peptide. More particularly, the present invention relates to a method for prevention or treatment of diabetic vascular leakage-induced diseases using C-peptide, a method for prevention or treatment of diabetic retinopathy, using C-peptide, and a composition for use in the prevention or treatment of the diseases, comprising C-peptide.

2. Description of the Related Art

As well known to those skilled in the art, Diabetes is a group of metabolic diseases with multiple etiologies, characterized by chronic hyperglycemia resulting from the absolute or functional deficiency of insulin activity. A high blood glucose level maintained for a long period of time causes a chronic metabolic disorder and causes damage to blood vessels, with the subsequent onset of various complications. These typically develop after 10 years of onset of diabetes because almost all organs of the body have been damaged. Particularly, abnormal vascular leakage is observed in diabetes patients, and diabetic vascular leakage induces various complications including diabetic retinopathy, diabetic neuropathy, diabetic nephropathy, diabetic vascular dysfunction, diabetic inflammation, etc.

These diabetic complications are relevant to the overexpression of VEGF (vascular endothelial growth factor). VEGF is likely to induce vascular leakage, and an increased level of VEGF in retinas of diabetes patients is known to induce angiogenesis and mascular edema. Further, a recent study has indicated that ROS generation and stress fiber formation interrupt VE-cadherin-based cell-cell adhesion at adherens junctions. Additionally, VE-cadherin is known as a requisite component to prevent the disassembly of blood vessel walls and to coordinate the passage of macromolecules through the endothelium.

Human C-peptide is a short peptide cleaved from proinsulin and is secreted in equimolar concentrations with insulin by pancreatic β-cells into the circulation. Deficiency of C-peptide, along with insulin, is a typical feature of type 1 diabetes mellitus as well as of the later stages of type 2 diabetes mellitus. Retinopathy is one of the major complications induced by diabetes and is the leading cause of blindness in adults. C-peptide is used for the diagnosis of diabetes, but there have been no reports on the application of C-peptide in the treatment of diabetic vascular leakage or secondhand diseases induced by diabetic vascular leakages.

From this background, the present inventors conducted intensive and thorough research into the treatment of diabetic vascular leakage, and found that C-peptide can be used for protecting VEGF-induced vascular leakage in diabetic retinopathy, leading to the present invention.

SUMMARY OF THE INVENTION

It is therefore a primary object of the present invention to provide a method or a composition for the prevention or treatment of diabetic vascular leakage-induced diseases using C-peptide.

It is another object of the present invention to provide a method or a composition for the prevention or treatment of diabetic retinopathy using C-peptide.

In accordance with an aspect thereof, the present invention provides a method for the prevention or treatment of diabetic vascular leakage-induced diseases, comprising administering an effective amount of C-peptide to an animal in need thereof.

In accordance with another aspect thereof, the present invention provides a pharmaceutical composition for the prevention or treatment of diabetic vascular leakage-induced diseases, comprising C-peptide as an active ingredient.

In accordance with a further aspect thereof, the present invention provides a method for the prevention or treatment of diabetic retinopathy, comprising administering an effective amount of C-peptide to an animal in need thereof.

In accordance with a still further aspect thereof, the present invention provides a pharmaceutical composition for the prevention or treatment of diabetic retinopathy, comprising C-peptide as an active ingredient.

Found to prevent vascular leakage by inhibiting VEGF-induced disassembly of VE-cadherin and, the pharmaceutical composition comprising C-peptide in accordance with the present invention has prophylactic or therapeutic applications to a broad spectrum of diabetic complications accompanied by vascular leakage.

BRIEF DESCRIPTION OF THE DRAWINGS

The above and other objects, features and advantages of the present invention will be more clearly understood from the following detailed description taken in conjunction with the accompanying drawings, in which:

FIG. 1A shows fluorescent images of the retina in which the square areas of upper panels are given as magnified images in lower panels of respective pictures. FIG. 1B is a graph in which retina permeability is quantified by measuring the fluorescence intensities of whole retina tissues (n=6), and expressed as mean±S.D. from six independent experiments. *$p<0.05$;

FIG. 2A is a graph of the levels of intracellular ROS determined using confocal microscopy after HUVECs were pre-incubated with 1 mM NAC, 0.5 mM Trolox, or 5 μM BAPTA-AM for 30 min, and stimulated with 10 ng/ml VEGF for 10 min, wherein data are expressed as mean±S.D. from three independent experiments. FIG. 2B is a graph in which ROS levels are plotted against C-peptide concentrations after HUVECs are pre-treated with various concentrations of C-peptide for 30 min and then stimulated with 10 ng/ml VEGF, showing that C-peptide inhibited the VEGF-induced generation of intracellular ROS in a dose-dependent manner. FIG. 2C is a graph of the levels of intracellular calcium ions in HUVECs labeled with 1 μM Fluo-4 AM as monitored over time by confocal microscopy at the single cell level (n=3);

FIG. 4A shows fluorescent images of VE-cadherin after VE-cadherin was stained and visualized using confocal microscopy (n=3). The scale bar represents 20 μm. FIG. 4B shows histograms of VE-cadherin in which adherens junctions are represented as indicated by dotted lines;

FIG. 5A shows fluorescent images of the retina (bar, 100 μm). FIG. 5B is a graph of retina permeability as quantitatively analyzed by measuring the fluorescence intensities of whole retina tissues (n=6). *p<0.01;

FIGS. 6B and 6C show that when administered by intradermal injection, C-peptide prevents VEGF-induced vascular leakage in the peripheral vessels of diabetic mice.

DESCRIPTION OF THE PREFERRED EMBODIMENTS

Figure 7:
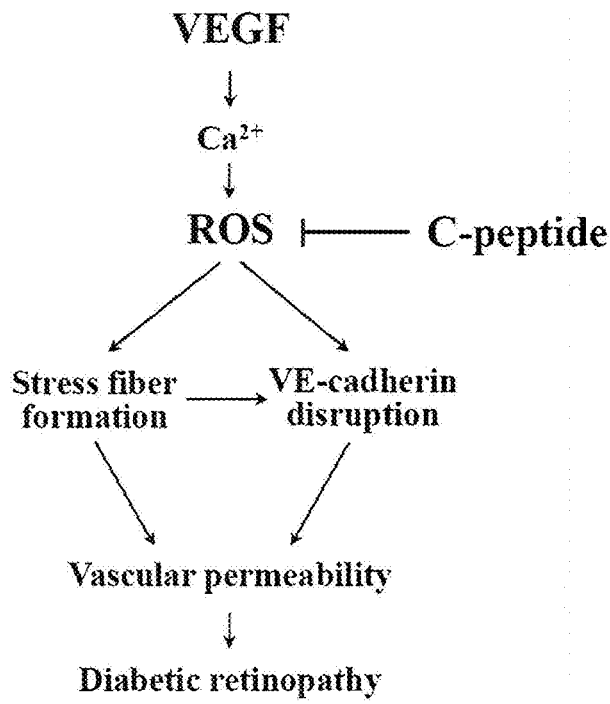
FIG. 7 is a schematic diagram of a possible signaling pathway involved in the C-peptide-mediated prevention of VEGF-induced vascular permeability, showing that C-peptide prevents VEGF-induced vascular leakage by inhibiting VEGF-induced ROS generation.

Leading to the present invention, intensive and thorough research into prevention and treatment of diabetes-induced vascular leakage in diabetes patients resulted in the finding that C-peptide inhibits VEGF-induced intracellular ROS generation with no effects on VEGF-induced intracellular calcium ion elevation, as opposed to VEGF that generates intracellular ROS through an increased influx of calcium ions into cells; C-peptide inhibits VEGF-induced stress fiber formation in endothelial cells as well as VEGF-induced disruption of VE-cadherin; and C-peptide prevents micro-vascular leakage in the retinas of diabetic mice by inhibiting VEGF-induced intracellular ROS generation, which stimulates stress fiber formation and disassembly of the adherens junction, resulting in micro-vascular permeability. The mechanism by which C-peptide inhibits diabetes-induced vascular leakage is illustrated in FIG. 7.

Thus, the present invention pertains to a method and a composition for the prevention or treatment of a diabetic vascular leakage-induced disease using C-peptide, and a method and a composition for the prevention or treatment of diabetic retinopathy.

In accordance with one aspect thereof, the present invention addresses a method and a composition for the prevention or treatment of diabetic vascular leakage using C-peptide.

More particularly, the present invention provides a method for prevention or treatment of a vascular leakage-induced disease, comprising administering an effective amount of C-peptide to an animal in need thereof. Also, the present invention provides a pharmaceutical composition for the prevention or treatment of a diabetic vascular leakage-induced disease, comprising C-peptide as an active ingredient.

As used herein, the term "C-peptide" refers to a short protein constituent of proinsulin, found in mammals and birds, which is produced by pancreatic β-cells in the islets of Langerhans. Its length varies from 21 to 31 amino acids depending on its source. Mammalian C-peptides from various mammals including dogs, cats, rats, chimpanzees, mice, cows, etc. as well as human C-peptide, and avian C-peptide from, for example, thrushes, fall within the scope of the present invention.

For instance, all the C-peptides originating from humans (*Homo sapiens*, SEQ ID NO: 1), rats (*Rattus norvegicus*, SEQ ID NO: 2) and chimpanzees (*Pan troglodytes*, SEQ ID NO: 3) are composed of 31 amino acids while C-peptide is found as a 29-mer peptide in mice (*Mus musculus*, SEQ ID NO: 4), as a 26-mer peptide in cow (*Bos taurus*, SEQ ID NO: 5), and as a 21-mer peptide in thrushes (*Turdus merula*, SEQ ID NO: 6) and red-footed boobies (*Sula sula*, SEQ ID NO: 7). The C-peptide of the present invention may have an amino acid sequence selected from the group consisting of SEQ ID NOS: 1 to 7.

For the purpose of the present invention, the C-peptide is employed as an active ingredient in the method or the composition provided by the present invention. The method or the composition may be applied to any animal that may be affected by a diabetic vascular leakage-induced disease as well as humans. In this context, C-peptide is preferably applied to animals of its origin. For example, if it is applied to humans, the method or the composition of the present invention preferably comprises the C-peptide of human origin (SEQ ID NO: 1).

In one embodiment of the present invention, C-peptide is found to suppress extravascular leak in diabetic model mice, so that C-peptide or a composition comprising C-peptide is applicable to the prevention or treatment of diabetic vascular leakage. In detail, the prophylactic or therapeutic effect of the method or composition of the present invention on diabetic vascular leakage-induced diseases may be attributed to C-peptide's inhibitory activity against intracellular ROS generation, without elevating intracellular calcium ion ($Ca^{2+}$) levels, against stress-fiber formation, and/or against disassembly of the adherens junction.

The prophylactic or therapeutic effect of C-peptide on diabetic vascular leakage can be applied to humans as well as any animal that could be affected by diabetes. In addition, resulting from inhibiting VEGF-induced disassembly of VE-cadherin, the effect can be applied not only to the retina, as will be demonstrated in the following Example section, but also to peripheral vessels of other tissues. That is, the diabetic vascular leakage may be retinal leakage or microvascular leakage in peripheral vessels of other tissues.

Accordingly, the method or composition of the present invention may be applied to the prevention or treatment of the vascular leakage following the onset of various diabetic complications, which occur in any diabetes patient, whether animal or human, and include diabetic retinopathy, diabetic neuropathy, diabetic nephropathy, diabetic vascular dysfunction, diabetic inflammation, etc.

The composition of the present invention is a pharmaceutical composition which may further comprise a pharmaceutically acceptable vehicle, excipient or diluent. The term "pharmaceutically acceptable vehicle, excipient or diluent," as used herein, is intended to include any and all solvents, dispersing media, coating agents, adjuvants, stabilizers, preservatives, anti-bacterial and fungal agents, isotonic agents, and absorption delaying agents. Examples of the vehicle, excipient or diluent useful in the present invention include lactose, dextrose, sucrose, sorbitol, mannitol, xylitol, maltitol, glucose, glycerin, acacia gum, alginage, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, etc.

Using a conventional method, the pharmaceutical composition of the present invention may be formulated into oral dosage forms such as powders, granules, tablets, capsules, suspensions, emulsions, syrups and aerosols, or into sterile injections. For the formulation of the composition according to the present invention, diluents or expedients, such as fillers, thickeners, binders, wetting agents, disintegrants, and surfactants, are commonly used. Solid formulations for oral dosage include tablets, pills, powders, granules, and capsules. These solid formulations are prepared with a lecithin-like emulsifier in combination with at least one expedient such as starch, calcium carbonate, sucrose, lactose, or gelatin.

In addition to the expedient, a lubricant, such as magnesium, stearate, talc, etc. can be used. Liquid formulations for oral administration include suspensions, internal solutions, emulsions, and syrups. In these liquid formulations, various expedients such as wetting agents, sweeteners, and preservatives, as well as simple diluents such as water and liquid paraffin may be contained. Formulations for non-oral dosage may be typified by sterile aqueous solution, non-aqueous solutions, suspensions, emulsions, lyophilized agents, and suppositories. For non-aqueous solutions and suspensions, vegetable oils such as propylene glycol, polyethylene glycol and olive oil, or injectable ester such as ethyloleate may be used.

So long as it leads to a target tissue, any administration route, whether orally or non-orally, may be adopted for the method or composition using C-peptide in accordance with the present invention. Preferable is subcutaneous injection using an osmotic pump, intradermal injection, intravenous injection, intraperitoneal injection or intravitreal injection.

In the present invention, C-peptide may be administered in an "effective amount," or a "pharmaceutically effective amount." The term "effective amount," or "pharmaceutically effective amount," as used herein, means an amount sufficient to afford a prophylactic or therapeutic effect without inducing a significant or undue immune response. It is determined depending on various factors known in the pharmaceutical or medical field, including the type and severity of disease, drug activity, administration route, discharge ratio, administration period of time, co-administered drugs, and others, patient's age, weight and sex, diet habit, health state, etc. Various factors that are taken into consideration in determining "effective amount," or "pharmaceutically effective amount" are known to those skilled in the art, and for instance, explained in Gilman et al., eds., Goodman And Gilman's: The Pharmacological Bases of Therapeutics, 8th ed., Pergamon Press, 1990, and Remington's Pharmaceutical Sciences, 17th ed., Mack Publishing Co., Easton, Pa., 1990.

The composition of the present invention may be administered alone or in combination with other therapeutics. The co-administration of the composition of the present invention and other therapeutics may be carried out simultaneously or sequentially. Single- or multi-dosages are possible. It is important to use the composition in as minimal an amount as possible, but in an amount that is sufficient enough to obtain the greatest therapeutic effect without causing side effects. In addition, the administration of the composition may be conducted using a device which helps the active ingredient direct toward target cells.

In accordance with another aspect thereof, the present invention addresses a method and a composition for the prevention or treatment of diabetic retinopathy, using C-peptide. More particularly, the present invention provides a method for prevention or treatment of diabetic retinopathy, comprising administering an effective amount of C-peptide to an animal in need thereof. Also, the present invention provides a pharmaceutical composition for the prevention or treatment of diabetic retinopathy, comprising C-peptide as an active ingredient.

As described above, C-peptide was found to suppress extravascular leak in diabetic model mice, so C-peptide or a composition comprising C-peptide is applicable to the prevention or treatment of diabetic retinopathy. The prophylactic or therapeutic effect of C-peptide on diabetic retinopathy can be applied to humans as well as any animal that could be affected by diabetes.

The terms "C-peptide" "dosage", "administration", and "effective amount (pharmaceutically effective amount)" used in the context of the prevention or treatment of diabetic retinopathy are as described in the previous aspect of the present invention.

Particularly, for the prevention or treatment of diabetic retinopathy, the composition of the present invention, or C-peptide may be administered at a single dose of from 2.4 µg to 60 µg and preferably at a single dose of 18 µg via an intrevitreal or interadermal route, or at a rate of from 1.45 pmol/kg/min to 36.5 pmol/kg/min using a mini-osmotic pump. However, the amount is not limited to those ranges, and may vary within the total daily dose, depending on a patient's age, weight, sex, health state and diet, the time of administration, the route of administration, the rate of excretion, and the severity of disease.

A better understanding of the present invention may be obtained through the following examples which are set forth to illustrate, but are not to be construed as limiting the present invention.

EXAMPLE 1

Preparation of Experiment

Example 1-1

Experimental Animals

Male C57BL/6 mice, six weeks old, were purchased from Nara Biotech (Seoul, Korea). The mice were maintained in temperature-controlled clean racks with a 12-h light/dark cycle. All experiments were performed in accordance with the guidelines of the Institutional Animal Care and Use Ethics Committee of Kangwon National University.

Example 1-2

Cell Culture

HUVECs were isolated from the human umbilical cord vein according to a well known process, and cells from passages 3 to 6 were used in the following experiments. Cells were inoculated into M199 culture media (supplemented with 20% FBS, 3 ng/ml bFGF, 5 U/ml heparin, 100 U/ml penicillin, and 100 μg/ml streptomycin) in 2% gelatin-coated coverslips, dishes, or plates, and grown at 37° C. in a humidified 5% $CO_2$ incubator.

For experiments, cells were incubated for 6 h in low-serum medium (M199 supplemented as above, but with only 1% FBS), and treated for a suitable time with 10 ng/ml VEGF in the presence or absence of various concentrations of C-peptide.

Example 1-3

Statistical Analysis

Data obtained in each Example was processes and graphically presented using Origin 6.1 (OriginLab, Northampton, Mass., USA). Statistical significance was determined using the t-test and ANOVA. A p-value of less than 0.05 was considered statistically significant.

EXAMPLE 2

Preventive Effect of C-Peptide Against Microvascular Leakage in Diabetic Model Animal VEGF levels increase in the retinas of diabetic animals and diabetic patients. Effects of C-peptide on retinal vascular leakage in streptozotocin diabetic mice with diabetic retinopathy were investigated.

Diabetic mice were generated by a single intraperitoneal injection of streptozotocin (150 mg/kg body weight) freshly prepared in 100 mM citrate buffer (pH 4.5). All mice were supplied with 10% sucrose overnight. Sufficient hyperglycemia was observed 2 days post-injection, as measured by the ACCU-CHEK® Active blood glucose monitor (Roche Diagnostics, Germany). One week after the streptozotocin injection, mice with non-fasting blood glucose levels greater than 16 mM, polyuria, and glucosuria were defined as diabetic and used for the experiments.

The diabetic mice were intravitreally injected with 2 μl of C-peptide (3.7 μg/ml) in PBS into one eye, and an equal volume of PBS was injected into the contralateral eye (n=6 per group). Normal (non-diabetic) mice were also intravitreally injected with 2 μl of PBS into eyes (Normal; n=6 per group). C-peptide concentrations in the vitreous chamber were maintained within the physiological range (0.9 to 2.0 nM) for 12 hrs after intravitreal injection.

After 24 hrs post injection, retina leakage was quantified using fluorescein angiography. In this regard, mice were injected with 1.25 mg of 500-kDa FITC-dextran (Sigma-Aldrich) into the left ventricle and the dye was allowed to circulate for 5 min. Eyes were enucleated and immediately fixed with 4% paraformaldehyde for 45 min. Retinas were dissected, cut in the Maltese cross-configuration, and flat-mounted onto slide glass. Retinas were observed using the confocal microscope. Retina leakage was quantitatively analyzed by determining the intensities of extravasated FITC-dextran from whole retina tissues (n=6 per group) using the FV-300 software.

Figure 1A:
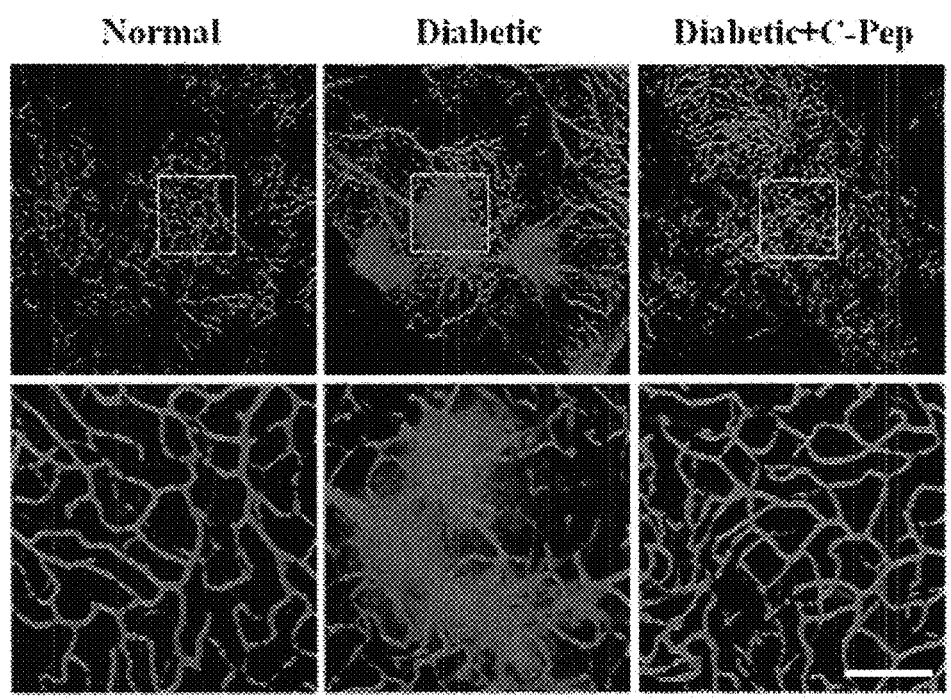
FIGS. 1A and 1B show the inhibitory activity of C-peptide against diabetes-induced vascular leakage, as measured in the retinas of Streptozotocin diabetic mice which were intravitreally injected with 2 μl of C-peptide (Diabetic+C-pep) into one eye, and an equal volume of PBS into the contralateral eye (Diabetic; n=6 per group), and normal (non-diabetic) mice which were also intravitreally injected with 2 μl of PBS into eyes (Normal; n=6 per group). Retinas were visualized by confocal microscopy.
Figure 1B:
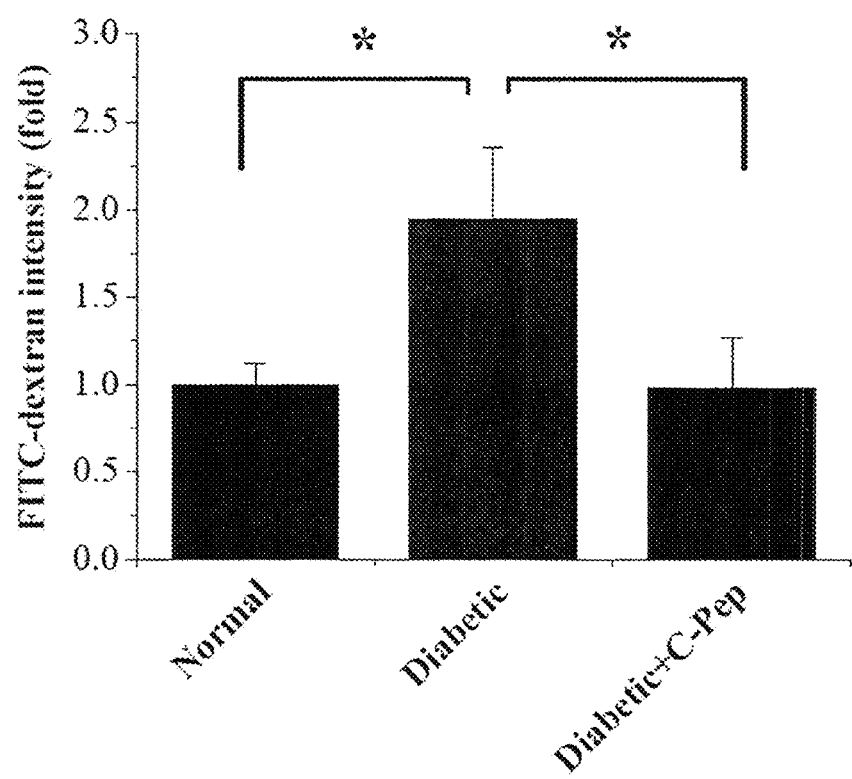

Results are shown in FIGS. 1A and 1B. FIGS. 1A and 1B demonstrate the inhibitory activity of C-peptide against diabetes-induced vascular leakage in photographs (a) and a graph (b). Diabetic mice were intravitreally injected with 2 μl of C-peptide (Diabetic+C-pep, n=6) into one eye, and an equal volume of PBS into the contralateral eye (Diabetic; n=6 per group). Normal (non-diabetic) mice were also intravitreally injected with 2 μl of PBS into eyes (Normal; n=6 per group). Retinas were visualized by confocal microscopy.

FIG. 1A shows representative fluorescent images of the retina. The square areas in upper panels are given as magnified images in lower panels of respective pictures. With reference to FIG. 1A, considerably high levels of extravasation of FITC-dextran were observed in the retinas of the diabetic mice (n=6), whereas this leakage was blocked in the retinas of the C-peptide-injected contralateral eyes (n=6; FIG. 1A).

FIG. 1B is a graph in which retina permeability is quantified by measuring the fluorescence intensities of whole retina tissues (n=6). Results are expressed as mean±S.D. from six independent experiments. *p<0.05. With reference to FIG. 1B, C-peptide prevention against vascular leakage in the retinas of diabetic mice was demonstrated as being quantitatively analyzed by determining the fluorescence intensity of FITC-dextran in whole retina tissues (n=6, p<0.05).

EXAMPLE 3

Effect of C-Peptide on Intracellular ROS (Reactive Oxygen Species) Generation and Calcium Ion Levels (1) Effect of C-Peptide on VEGF-Induced Intracellular ROS Generation In diabetes, elevated VEGF expression in retinal endothelial cells is involved in retinal vascular leakage through the generation of intracellular ROS. In this context, an examination was made of the protective effect of C-peptide against VEGF-induced ROS generation and thereby the prevention of vascular leakage, using HUVECs.

In detail, HUVECs inoculated into coverslips were treated with VEGF and C-peptide, and incubated with 10 μM 2',7'-dichlorodihydrofluorescein diacetate (Molecular Probes, Eugene, Oreg.) in phenol red-free media for the last 10 min. The coverslips were mounted on a perfusion chamber, and labeled cells were rapidly scanned by confocal microscopy. The level of intracellular ROS was determined by comparing the fluorescence intensities of treated cells with those of control cells, and expressing this as a fold difference.

Figure 2A:
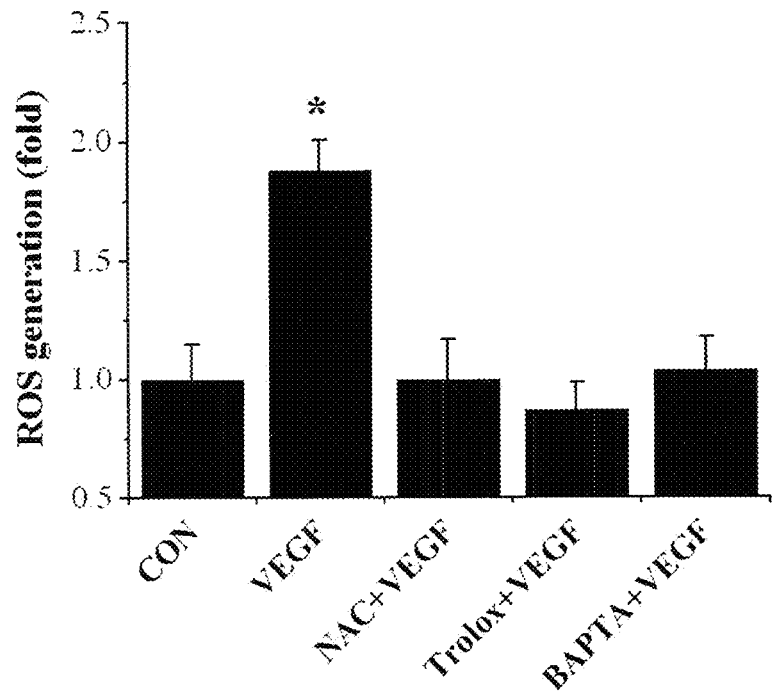
FIGS. 2A and 2B show that C-peptide inhibits VEGF-induced ROS generation but has no effect on intracellular calcium ions.
Figure 2B:
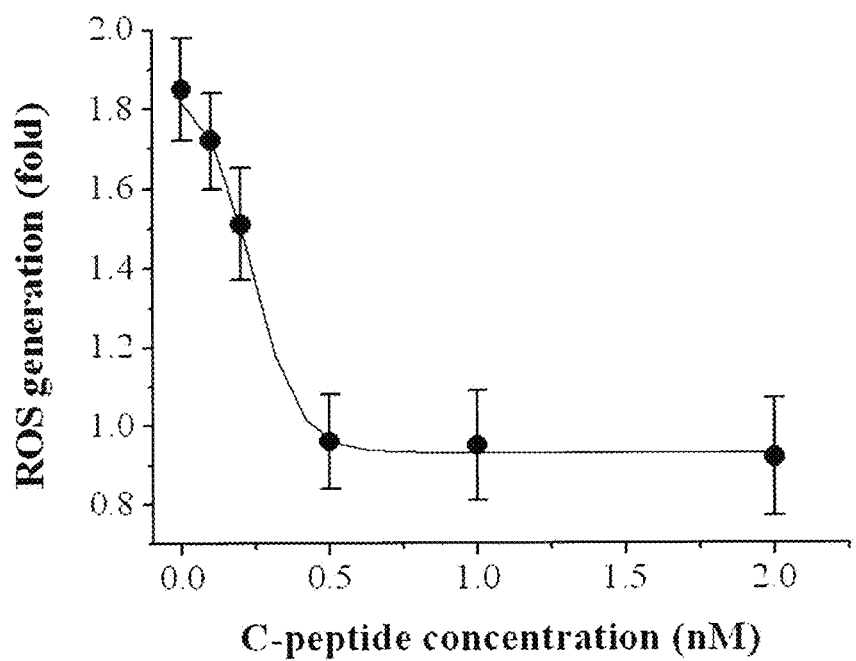

Results are given in FIGS. 2A and 2B. FIGS. 2A and 2B show that C-peptide inhibits VEGF-induced ROS generation but has no effect on intracellular calcium ions. FIG. 2A is a graph of the levels of intracellular ROS determined using confocal microscopy after HUVECs were pre-incubated with 1 mM NAC, 0.5 mM Trolox, or 5 µM BAPTA-AM (1,2-bis(2-aminophenoxy)ethane-N,N,N-',N'-tetraacetic acid tetrakis(acetoxymethyl ester)) for 30 min, and stimulated with 10 ng/ml VEGF for 10 min. Data are expressed as mean±S.D. from three independent experiments. As previously reported, VEGF generated intracellular ROS ($p<0.01$), and this ROS generation was abolished by treatment with the ROS scavengers Trolox and NAC (N-acetyl-L-cysteine) (FIG. 2A). Meanwhile, the $Ca^{2+}$ chelator BAPTA-AM also blocked VEGF-induced intracellular ROS generation, indicating that VEGF produces intracellular ROS by elevating intracellular $Ca^{2+}$.

FIG. 2B is a graph in which ROS levels are plotted against C-peptide concentrations after HUVECs are pre-treated with various concentrations of C-peptide for 30 min and then stimulated with 10 ng/ml VEGF. As can be seen in data of FIG. 2B, C-peptide inhibited the VEGF-induced generation of intracellular ROS in a dose-dependent manner, with complete prevention observed at 0.5 nM ROS.

(2) Effect of C-Peptide on VEGF-Induced Intracellular $Ca^{2+}$ Elevation

To monitor intracellular $Ca^{2+}$ levels, cells inoculated into coverslips were incubated with 1 µM Fluo-4 AM for 30 min. The coverslips were mounted on perfusion chambers and scanned every 10 sec by confocal microscopy (FV-300). Serial images from the scan were processed to analyze changes in intracellular $Ca^{2+}$ levels at the single-cell level. Data were expressed as the relative fluorescence intensity (RFI).

Results are shown in FIG. 2C. FIG. 2C is a graph of the levels of intracellular calcium ions in HUVECs labeled with 1 µM Fluo-4 AM as monitored over time by confocal microscopy at the single cell level (n=3). As is understood from data of FIG. 2C, VEGF induced a rapid increase in intracellular $Ca^{2+}$ and the elevated intracellular $Ca^{2+}$ level was maintained until 600 sec. As expected, BAPTA-AM blocked changes in intracellular $Ca^{2+}$ levels in response to VEGF. In contrast, C-peptide did not increase intracellular $Ca^{2+}$ (FIG. 2C) and had no effect on VEGF-induced changes in intracellular $Ca^{2+}$.

From the data, it is understood that VEGF generates intracellular ROS by elevating intracellular $Ca^{2+}$ levels whereas C-peptide inhibits the VEGF-induced elevation of intracellular ROS without affecting intracellular $Ca^{2+}$ levels.

EXAMPLE 4

Effect of C-Peptide on VEGF-Induced Stress Fiber Formation

VEGF activates stress fiber formation, and the disruption of VE-cadherin based adherens junction integrity, resulting in vascular leakage. In this regard, an examination was made of the effect of C-peptide on VEGF-induced stress formation and VEGF-induced disassembly of the adherens junction.

Elevation of VEGF levels in retinal endothelial cells can induce stress fiber formation through increased ROS generation. To investigate the protective role of C-peptide in VEGF-induced stress fiber formation, actin filaments were visualized in HUVECs by staining with rhodamine-phalloidin.

HUVECs were grown on gelatin-coated round coverslips in 12-well culture plates, and incubated with 10 ng/ml C-peptide or 0.5 mM VEGF, alone or in combination, or with 10 ng/ml VEGF in the presence of an ROS scavenger, that is, 1 mM NAC or 0.5 mM Trolox for 1 hr at 37° C. The cells were rapidly rinsed with PBS and fixed with 3.7% formaldehyde in PBS for 30 min. Then, the cells were permeabilized with 0.2% Triton X-100 in PBS for 30 min, and stained with rhodamine-palloidin (Molecular Probes) in PBS for 1 h. The resulting stained cells were mounted on a glass slide using a mounting solution, followed by visualizing actin filaments by confocal microscopy.

Figure 3:
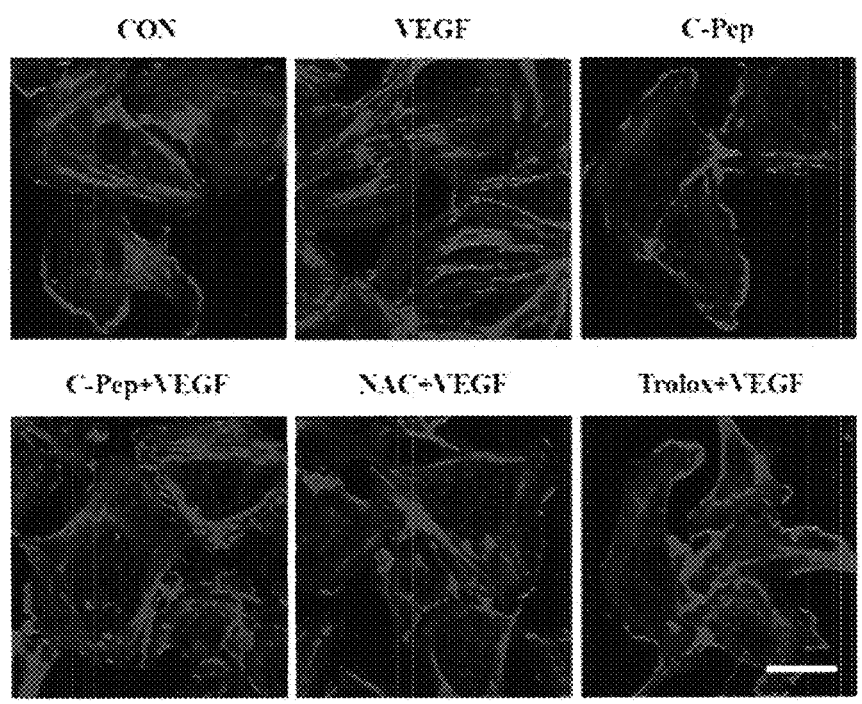
FIG. 3 shows fluorescent photographs of HUVECs, demonstrating that C-peptide inhibits VEGF-induced stress fiber formation and VEGF-induced disassembly of adherens junction. The inhibitory activity of C-peptide against VEGF-induced stress fiber formation, as shown in FIG. 1, was observed after HUVECs were incubated for 1 hr with 10 ng/ml VEGF or 0.5 nM C-peptide alone, or with 10 ng/ml VEGF in the presence of 0.5 nM C-peptide, 1 mM NAC, or 0.5 mM Trolox. Microfilaments were stained with rhodamine-phalloidin and observed by confocal microscopy (n=3). Scale bar represents 30 μm.

Results are given in FIG. 3. FIG. 3 shows fluorescent photographs of HUVECs, demonstrating that C-peptide inhibits VEGF-induced stress fiber formation and VEGF-induced disassembly of adherens junction. FIG. 3 shows the inhibitory activity of C-peptide against VEGF-induced stress fiber formation. HUVECs were incubated for 1 hr with 10 ng/ml VEGF or 0.5 nM C-peptide alone, or with 10 ng/ml VEGF in the presence of 0.5 nM C-peptide, 1 mM NAC, or 0.5 mM Trolox. Microfilaments were stained with rhodamine-phalloidin and observed by confocal microscopy (n=3). Scale bar represents 30 µm. With reference to FIG. 3, VEGF activated the formation of stress fibers, which was sufficiently suppressed by treatment with C-peptide. VEGF-activated stress fiber formation was also inhibited upon treatment with the ROS scavengers NAC and Trolox, indicating that intracellular ROS is essential for the VEGF-induced formation of stress fibers.

When the data obtained in Example 2, that is, the inhibition of VEGF-stimulated ROS generation by C-peptide is taken into consideration, these results demonstrate that C-peptide inhibits VEGF-induced stress fiber formation by preventing intracellular ROS generation.

EXAMPLE 5

Effect of C-Peptide on Disassembly of Adherens Junction (1) Effect of C-Peptide on Disassembly of Adherens Junction in HUVECs To reveal the mechanism involved in C-peptide protection against diabetes-induced vascular leakage, an examination was made of the effect of C-peptide on VEGF-induced changes in the adherens junction protein VE-cadherin in HUVECs.

Confluent cell layers (HUVECs) in 6-well plates were incubated with C-peptide or an ROS scavenger for 30 min, and then treated with VEGF for 90 min at 37° C. The treated cells were rinsed with PBS, and fixed with 3.7% formaldehyde in PBS for 30 min. The cells were permeabilized with 0.2% Triton X-100 in PBS for 30 min, and stained overnight at 4° C. with a monoclonal VE-cadherin antibody (Santa Cruz Biotechnology, Santa Cruz, Calif.) in PBS. Thereafter, the cells were probed with goat anti-mouse FITC (fluorescein isothiocyanate; Sigma, St. Louis, Mo.), followed by visualizing VE-cadherin by confocal microscopy.

Figure 4A:
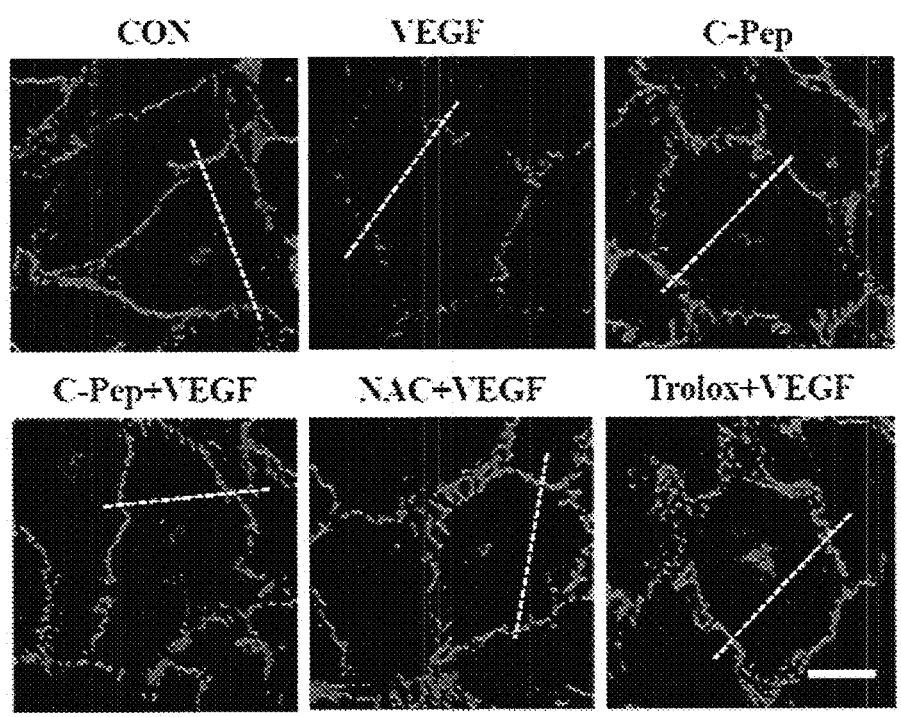
FIGS. 4A and 4B show the inhibitory activity of C-peptide against the VEGF-induced disruption of adherens junctions, as measured after HUVECs were incubated for 90 min with 10 ng/ml VEGF or 0.5 nM C-peptide alone, or with 10 ng/ml VEGF in the presence of 0.5 nM C-peptide, 1 mM NAC, or 0.5 mM Trolox (n=3).
Figure 4B:
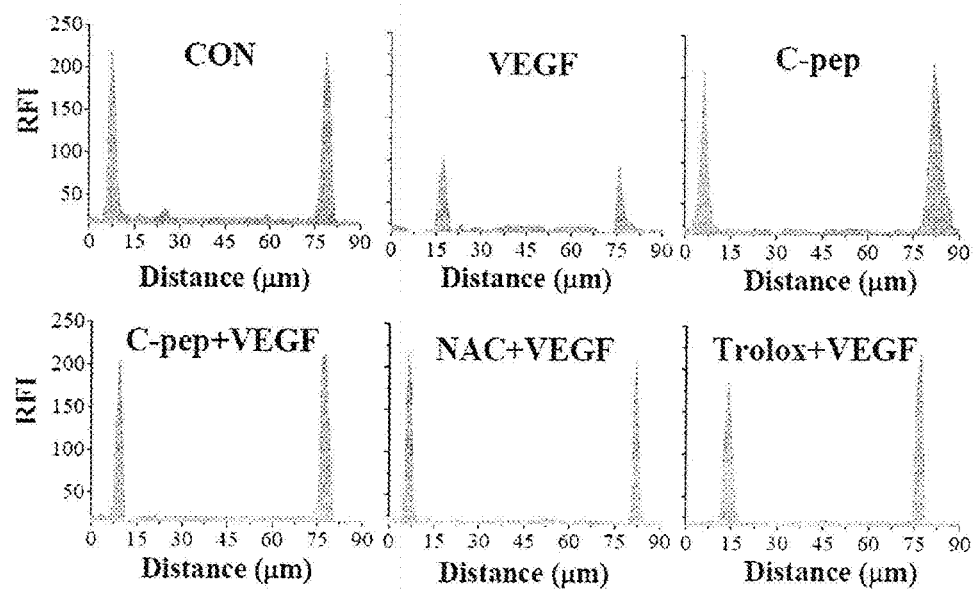

Results are shown in FIGS. 4A and 4B. FIGS. 4A and 4B show the inhibitory activity of C-peptide against the VEGF-induced disruption of the adherens junctions. HUVECs were incubated for 90 min with 10 ng/ml VEGF or 0.5 nM C-peptide alone, or with 10 ng/ml VEGF in the presence of 0.5 nM C-peptide, 1 mM NAC, or 0.5 mM Trolox (n=3), after which VE-cadherin was stained and visualized using confocal microscopy (n=3). The scale bar represents 20 μm.

Referring to FIG. 4A, VEGF stimulated the disassembly of VE-cadherin, and this disassembly was inhibited by C-peptide. The VEGF-induced disassembly of VE-cadherin was also prevented by NAC and Trolox, indicating that intracellular ROS mediates the VEGF-induced disruption of VE-cadherin.

With reference to FIG. 4B, there are histograms in which changes in permeability resulting from the disassembly of VE-cadherin are represented by relative fluorescence intensities (RFI). As can be seen in FIG. 4B, the VEGF-induced decrease in the fluorescence intensity of the adherens junctions was recovered by treatment with C-peptide and ROS scavengers. Thus, C-peptide protects against VEGF-induced disassembly of VE-cadherin at cell junctions by inhibiting intracellular ROS generation in endothelial cells.

(2) Effect of C-Peptide on Disassembly of Adherens Junction in Retina

Diabetic mice were intravitreally injected with 2 μl C-peptide into one eye (Diabetic+C-Pep) and an equal volume of PBS into the contralateral eye (Diabetic, n=3). Normal (non-diabetic) mice also were intravitreally injected with 2 μl PBS into eyes (Normal, n=3).

VE-cadherin was stained in the retina and visualized using confocal microscopy as described below.

Microvessels were stained for VE-cadherin in retinal whole mounts. In detail, isolated retinas were fixed in 100% ethanol for 30 min, delipidated in 100% ice-cold acetone for 10 min, and permeabilized with 0.3% Triton X-100 for 1 hr. The retinas were incubated with an anti-VE-cadherin antibody (Enzo Life Sciences, Farmingdale, N.Y., USA) at 4° C. for 24 hrs, and probed with goat anti-mouse FITC (Sigma) at 4° C. for 24 hrs, followed by visualizing VE-cadherin by confocal microscopy (FV-300, Olympus).

Figure 4C:
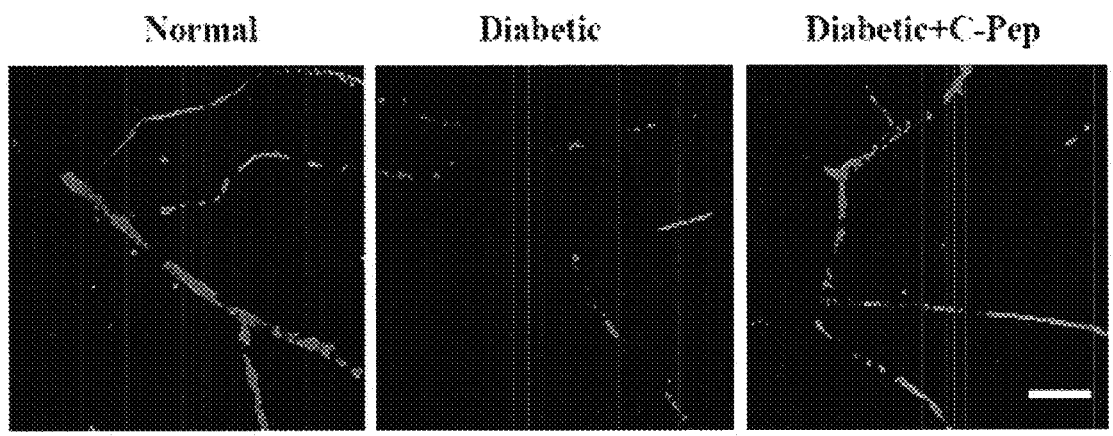
FIG. 4C shows that C-peptide recovers hyperglycemia-induced disruption of adherens junctions in the retina of diabetic mice. Diabetic mice were intravitreally injected with 2 μl C-peptide into one eye (Diabetic+C-Pep) and an equal volume of PBS into the contralateral eye (Diabetic, n=3). Non-diabetic mice also were intravitreally injected with 2 μl PBS into eyes (Normal, n=3). VE-cadherin was stained in the retina and visualized using confocal microscopy (n=3). Bar, 30 μm.

Results are shown in FIG. 4C. Consistent with the preventive effect of C-peptide against VEGF-induced disassembly of VE-cadherin in HUVECs, as seen in FIG. 4C, the intravitreal injection of C-peptide inhibited the diabetes-induced disassembly of adherens junctions in the microvessels of the diabetic mouse retina.

Therefore, C-peptide protects against VEGF-induced disassembly of VE-cadherin at cell junctions by inhibiting intracellular ROS generation in endothelial cells.

EXAMPLE 6

Inhibitory Activity of C-Peptide Against Microvascular Leakage in Retinas of Diabetic Mice From the in vitro findings in cultured endothelial cells, it was demonstrated that C-peptide protects against VEGF-induced disassembly of adherens junctions by inhibiting intracellular ROS generation as well as stress fiber formation. It is also reported that VEGF levels increase in the retinas of diabetic animals and diabetic patients. To confirm the in vitro findings, the effect of anti-VEGF antibodies and ROS scavengers on retinal vascular leakage in streptozotocin diabetic mice was investigated.

Diabetic mice were intravitreally injected with a monoclonal VEGF antibody (100 μg/ml), N-acetyl-cysteine (81.5 mg/ml), or Trolox (125 μg/ml) into one eye, and an equal volume of PBS was injected into the contralateral eye (n=6 per group). Twenty four hrs post-injection, retinal vascular leakage was quantified using fluorescein angiography. For the experiment, mice were injected with 1.25 mg of 500-kDa FITC-dextran (Sigma) into the left ventricle and the dye was allowed to circulate for 5 min. The eyes were enucleated and immediately fixed with 4% paraformaldehyde for 45 min. Retinas were dissected, cut in the Maltese cross-configuration, and flat-mounted onto slide glass before observation using confocal microscopy. Retinal vascular leakage was quantitatively analyzed by determining the intensities of extravasated FITC-dextran from whole retina tissues (n=6 per group) using confocal microscopy (FV-300, Olympus, Tokyo, Japan), and applying the intensity data to the FV-300 software.

Figure 5A:
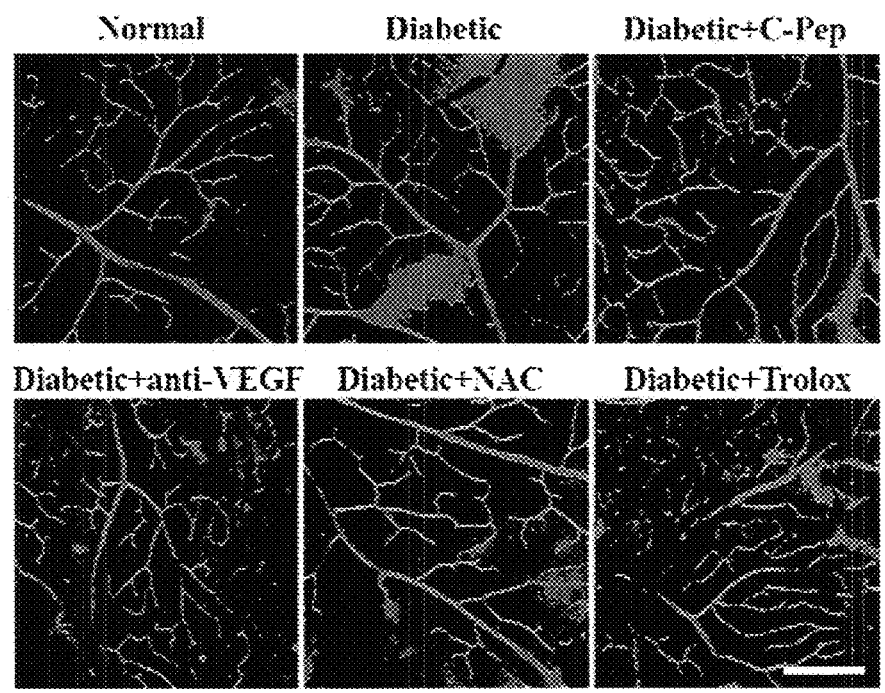
FIGS. 5A and 5B show that anti-VEGF and ROS scavengers prevent against vascular leakage in retinas of diabetic mice. In this regard, diabetic mice were intravitreally injected with 2 μl C-peptide (Diabetic+C-Pep), anti-VEGF (Diabetic+anti-VEGF), N-acetyl-cysteine (Diabetic+NAC), and Trolox (Diabetic+Trolox) into one eye, and an equal volume of PBS into the contralateral eye (Diabetic; n=6 per group). Normal (non-diabetic) mice were also intravitreally injected with 2 μl PBS into the eyes (Normal; n=6 per group). Retinas were visualized by confocal microscopy.
Figures 5B, 6A:
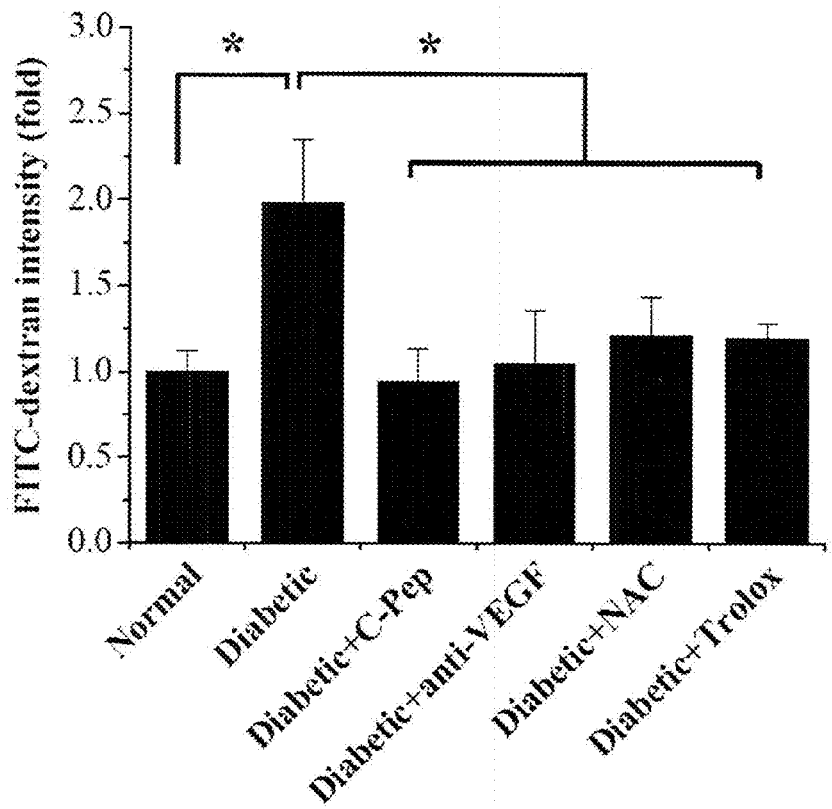
FIG. 6A shows serum C-peptide levels left after injection into mice by an osmotic pump.

Results are shown in FIGS. 5A and 5B. As can be seen in FIG. 5A, intravitreal injection of a monoclonal anti-VEGF antibody significantly inhibited microvascular leakage in the retinas of diabetic mice, demonstrating that VEGF is involved in retinal vascular leakage in diabetic mice. Intravitreal injection of the ROS scavengers NAC and Trolox also prevented retinal vascular leakage in diabetic mice. As expected, extravasation of FITC-dextran in the retinas of diabetic mice was also blocked by C-peptide injection. The prevention of C-peptide against retinal vascular leakage in diabetic mice was quantitatively analyzed by determining the fluorescence intensity of FITC-dextran in whole retina tissues (n=6, $p<0.01$), and the results are graphically given in FIG. 5B.

As is understood from data of FIG. 5B, C-peptide protects against VEGF-induced retinal vascular leakage by inhibiting intracellular ROS generation in retinal endothelial cells.

EXAMPLE 7

Effect of C-Peptide According to Injection Routes (1) Subcutaneous Injection Using Osmotic Pump After implantation of a mini-osmotic pump for delivering C-peptide, blood c-peptide levels were measured. One group of diabetic mice (n=7) was subcutaneously implanted with ALZET® mini-osmotic pump 2004 (DURECT, Cupertino, Calif.) containing C-peptide in PBS with a delivery rate of 35 pmol/min/kg. The other diabetic (n=7) and control groups (n=7) underwent sham operations. During the continuous subcutaneous C-peptide perfusion, serum C-peptide levels were measured using a C-peptide Enzyme Immunoassay Kit (RayBiotech, Norcross, Ga.).

Results are summarized in FIG. 6A. FIG. 6A shows serum C-peptide levels left after injection into mice by an osmotic pump. As is understood from the data of FIG. 6A, the serum C-peptide level was elevated to a normal value. Hence, a mini-osmotic pump makes it possible to conduct subcutaneous injection at a delivery rate of from 1.45 pmol/kg/min to 36.5 pmol/kg/min.

(2) Intradermal Injection

The preventive effect of C-peptide against microvascular leakage was supported by an in vivo Miles vascular permeability assay in the skin of streptozotocin diabetic mice.

A Miles vascular permeability assay was performed in diabetic mice as follows. After 2 to 3 days post-shaving, mice were anesthetized and intravenously injected with 150 μl of a 1% Evans blue solution. After 15 min, 15 μl of a VEGF (10 ng) solution containing 0, 7.5, or 15 ng of C-peptide was injected intradermally into the shaved skin of the mice (n=12 per group). PBS was injected for the control (n=12). An area of skin that included the blue spot resulting from leakage of the dye was dissected, and the Evans blue dye was eluted from the dissected skin by incubation with formamide at 56° C. for 2 days. The amount of dye was quantitated by spectrophotometry at 620 nm.

Figure 6B:
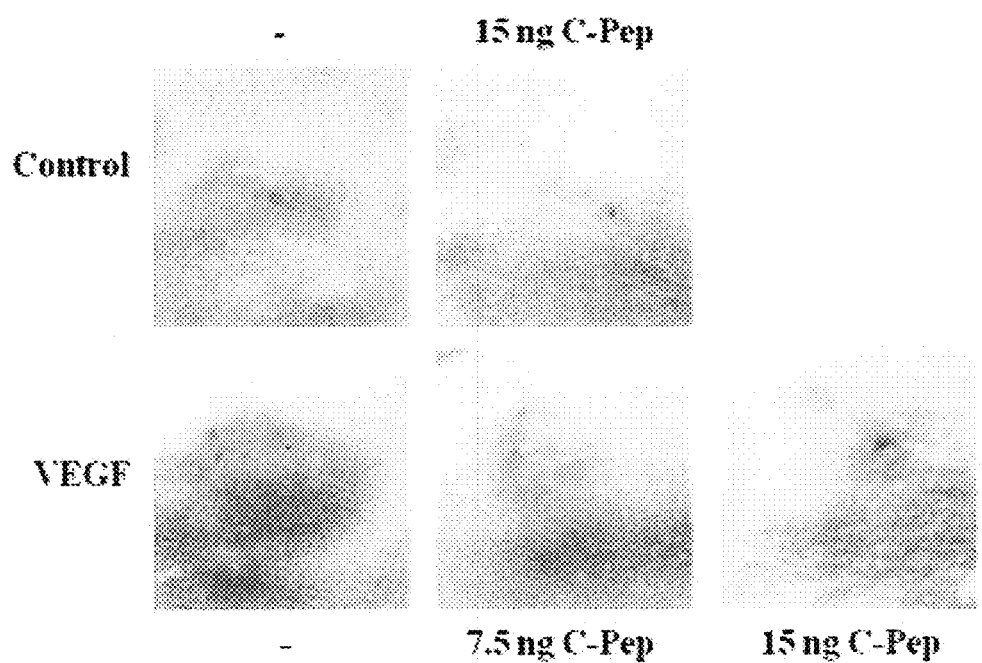

Results are shown in FIGS. 6B and 6C. FIG. 6B shows representative images of mouse groups treated with or without VEGF alone or in combination with various amounts of C-peptide. FIG. 6C is a graph of the Evans blue dye contents eluted from the dissected skin as quantitated compared to the control (n=12). *p<0.01. As is apparent from the data of FIG. 6B, intradermal injection of VEGF significantly induced vascular permeability in diabetic mice, which was suppressed by C-peptide in a dose-dependent manner. However, C-peptide alone did not cause a significant change in vascular permeability. The VEGF-induced vascular leakage of Evans blue dye from plasma into the interstitial space was quantified in skin-core biopsies by dye extraction and spectrophotometric absorbance measurements (n=12, p<0.01; FIG. 6C). These results demonstrate C-peptide prevention of microvascular leakage in peripheral vessels of streptozotocin diabetic mice. Taken together, the data obtained above indicate that C-peptide prevents microvascular leakage in the retinas of diabetic mice by inhibiting VEGF-induced intracellular ROS generation, which stimulates stress fiber formation and disassembly of the adherens junction, resulting in micro-vascular permeability.

(3) Intravitreal Injection

After intravitreal injection, C-peptide levels in the vitreous fluid were monitored with time. In this regard, C-peptide was intravitreally injected at a dose of 7.5 ng, after which C-peptide in the vitreous chamber was quantitated using a human C-peptide ELISA kit (Millipore Co. Billerica, Mass.) (n=4).

Figure 6D:
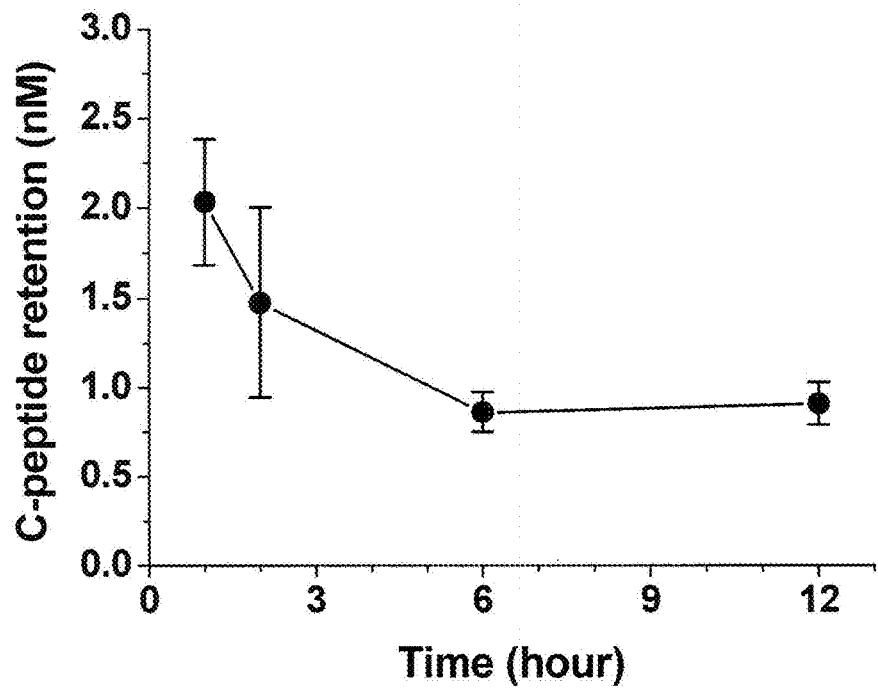
FIG. 6D is a graph in which serum C-peptide levels are plotted against time after intravitreal injection.

Results are given in FIG. 6D. Intravitreal injection of C-peptide was previously found to prevent retinal leakage 24 hrs post-injection. As shown in FIG. 6D, the vitreous chamber maintained a normal level of C-peptide until about 12 hrs after intravitreal injection. That is, it is understood from the data of FIG. 6D that a normal intravitreal C-peptide level was maintained upon intravitreal injection, thereby suppressing VEGF-induced retinal leakage.

Taking the data together, it is concluded that C-peptide prevents microvascular leakage in the retinas of diabetic mice by inhibiting VEGF-induced intracellular ROS generation, which stimulates stress fiber formation and disassembly of the adherens junction, resulting in micro-vascular permeability Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treatment of a diabetic vascular leakage-induced disease in an animal in need thereof, comprising administering a dose of between 2.4 µg and 60 µg of C-peptide consisting of an amino acid sequence selected from the group consisting of SEQ ID NOS: 1 to 7, wherein the C-peptide exhibits at least one of inhibitory activity against intracellular ROS generation without elevating intracellular calcium ion (Ca2+) levels, inhibitory activity against stress-fiber formation, and inhibitory activity against disassembly of adherens junction in said animal, wherein the diabetic vascular leakage-induced disease is selected from the group consisting of diabetic retinopathy, diabetic neuropathy, diabetic nephropathy, diabetic vascular dysfunction, diabetic inflammation, and a combination thereof, and wherein the diabetic vascular leakage is retinal leakage.

2. The method of claim 1, wherein the C-peptide is administered by subcutaneous injection using an osmotic pump, intradermal injection, intravenous injection, intraperitoneal injection, or an intravitreal injection.

3. The method of claim 1, wherein the animal is a human.

4. A method for treatment of diabetic retinopathy in an animal in need thereof, comprising administering a dose of between 2.4 µg and 60 µs of C-peptide consisting of an amino acid sequence selected from the group consisting of SEQ ID NOS: 1 to 7, wherein the C-peptide exhibits at least one of inhibitory activity against intracellular ROS generation without elevating intracellular calcium ion (Ca2+) levels, inhibitory activity against stress-fiber formation, and inhibitory activity against disassembly of adherens junction in said animal.

5. The method of claim 4, wherein the C-peptide is administered by subcutaneous injection using an osmotic pump, intradermal injection, intravenous injection, intraperitoneal injection, or an intravitreal injection.

6. The method of claim 4, wherein the animal is a human.

7. The method of claim 4, wherein the dose is administrated through at least one of an intravitreal route and an intradermal route.

8. The method of claim 4, wherein the dose is administrated using an osmotic pump at a rate of from 1.45 pmol/kg/min to 36.5 pmol/kg/min.

9. The method of claim 4, comprising administering the C-peptide in a dose of 18 μg.

* * * * *